US009925139B2

(12) United States Patent
Skrtic et al.

(10) Patent No.: US 9,925,139 B2
(45) Date of Patent: Mar. 27, 2018

(54) PHARMACEUTICAL COMPOSITIONS FOR ACUTE GLUCOCORTICOID THERAPY

(75) Inventors: Stanko Skrtic, Gotegorg (SE); Jörgen Johnsson, Helsingborg (SE); Hans Lennernäs, Uppsala (SE); Thomas Hedner, Gallstad (SE); Gudmundur Johannsson, Vastra Frolunda (SE)

(73) Assignee: ACUCORT AB, Helsingborg (SE)

( * ) Notice: Subject to any disclaimer, the term of this patent is extended or adjusted under 35 U.S.C. 154(b) by 1349 days.

(21) Appl. No.: 11/587,512

(22) PCT Filed: Apr. 21, 2005

(86) PCT No.: PCT/EP2005/004399
§ 371 (c)(1),
(2), (4) Date: Mar. 7, 2008

(87) PCT Pub. No.: WO2005/102287
PCT Pub. Date: Nov. 3, 2005

(65) Prior Publication Data
US 2009/0035375 A1    Feb. 5, 2009

Related U.S. Application Data

(60) Provisional application No. 60/564,206, filed on Apr. 22, 2004.

(30) Foreign Application Priority Data

Apr. 22, 2004   (SE) ...................... 0401032

(51) Int. Cl.
| A61K 9/14 | (2006.01) |
| A61K 9/08 | (2006.01) |
| A61K 9/20 | (2006.01) |
| A61K 9/12 | (2006.01) |
| A61K 9/16 | (2006.01) |
| A61K 9/50 | (2006.01) |
| A61K 9/00 | (2006.01) |
| A61K 9/70 | (2006.01) |
| A61K 31/573 | (2006.01) |
| A61K 31/00 | (2006.01) |

(52) U.S. Cl.
CPC ............ *A61K 9/0095* (2013.01); *A61K 9/006* (2013.01); *A61K 9/2018* (2013.01); *A61K 9/5078* (2013.01); *A61K 9/7007* (2013.01); *A61K 31/00* (2013.01); *A61K 31/573* (2013.01)

(58) Field of Classification Search
None
See application file for complete search history.

(56) References Cited

U.S. PATENT DOCUMENTS

| 4,448,774 | A |   | 5/1984 | Clemente et al. |
| 4,713,243 | A | * | 12/1987 | Schiraldi ............... A61K 9/006 424/435 |
| 4,765,983 | A | * | 8/1988 | Takayanagi ............ A61K 31/57 424/434 |
| 5,059,426 | A | * | 10/1991 | Chiang ................ A61K 9/0014 424/447 |
| 5,061,493 | A |   | 10/1991 | Ayache et al. |
| 5,192,528 | A | * | 3/1993 | Radhakrishnan et al. ...... 424/45 |
| 5,298,256 | A | * | 3/1994 | Flockhart ............... A61K 38/11 424/435 |
| 5,658,956 | A | * | 8/1997 | Martin et al. ................. 514/724 |
| 5,858,410 | A | * | 1/1999 | Muller et al. ................. 424/489 |
| 5,948,430 | A | * | 9/1999 | Zerbe ................... A61K 8/0208 424/435 |
| 6,143,353 | A | * | 11/2000 | Oshlack et al. ............. 427/2.21 |
| 6,303,147 | B1 | * | 10/2001 | Gilis ............................. 424/484 |
| 6,375,963 | B1 | * | 4/2002 | Repka ..................... A61K 9/006 424/402 |
| 6,428,814 | B1 | * | 8/2002 | Bosch .................... A01N 25/12 424/501 |
| 2001/0006677 | A1 | * | 7/2001 | McGinity ............ A61K 9/0007 424/449 |
| 2002/0127190 | A1 | * | 9/2002 | Zerbe ................... A61K 8/0208 424/49 |
| 2003/0044446 | A1 | * | 3/2003 | Moro et al. .................... 424/426 |

(Continued)

FOREIGN PATENT DOCUMENTS

| EP | 0311540 |   | 4/1989 |
| EP | 0745382 | A | 12/1996 |
| FR | 2209585 | A | 7/1974 |

(Continued)

OTHER PUBLICATIONS

Mamata Singh, Rohit Sharma, U.C. Banerjee. Biotechnological applications of cyclodextrins. Biotechnology Advances 20 (2002) 341-359.*

V. G. Belikov, E. V. Kompantseva, and Yu. K. Botezat-Belyi. Cyclodextrins and Their Inclusion Compounds With Drugs (Review). Translated from Khimlko-farmatsevticheskii Zhurnal, vol. 20, No. 5, pp. 525-532, May 1986.*

Harmik Sohi, Yasmin Sultana, and Roop K. Khar. Taste Masking Technologies in Oral Pharmaceuticals: Recent Developments and Approaches. Drug Development and Industrial Pharmacy vol. 30, No. 5, pp. 429-448, 2004.*

V. G. Belikov, E. V. Kompantseva, and Yu. K. Botezat-Belyi. Cyclodextrins and Their Inclusion Compounds With Drugs (Review). Translated from Khimlko-farmatsevticheskii Zhurnal, vol. 20, No. 5, pp. 525-532, May 1986. Original article submitted Apr. 2, 1985.*

(Continued)

Primary Examiner — Isaac Shomer
Assistant Examiner — Michael P Cohen
(74) Attorney, Agent, or Firm — Foley & Lardner LLP

(57) ABSTRACT

The present invention relates to glucocorticoid-containing pharmaceutical compositions or kits for use in acute emergency situations where acute glucocorticoid therapy is required. Notably, the invention relates to pharmaceutical compositions and kits that are designed to be administered by non-medically trained persons outside a hospital or another medical or clinical setting. The invention also relates to a method for treating a disorder requiring acute glucocorticoid therapy by providing a fast onset of action of a glucocorticoid.

41 Claims, 12 Drawing Sheets

(56) References Cited

U.S. PATENT DOCUMENTS

2003/0119786 A1* 6/2003 Keith .................. A61K 31/519
514/81
2003/0143277 A1* 7/2003 Ameye et al. ................ 424/487

FOREIGN PATENT DOCUMENTS

| GB | 1458676 A | 12/1976 | | |
|---|---|---|---|---|
| WO | WO 87/05804 | 10/1987 | | |
| WO | WO 90/03776 | 4/1990 | | |
| WO | WO 90/06136 | 6/1990 | | |
| WO | WO 92/11001 A | 7/1992 | | |
| WO | WO 97/38662 | 10/1997 | | |
| WO | WO 97/46243 | 12/1997 | | |
| WO | WO 98/48782 A | 11/1998 | | |
| WO | WO 99/40898 | 8/1999 | | |
| WO | WO 00/10530 | 3/2000 | | |
| WO | WO 02/39555 | 5/2002 | | |
| WO | WO 0241920 A1 * | 5/2002 | ........... | A61K 9/0056 |
| WO | WO 02/072033 | 9/2002 | | |
| WO | WO 02/076425 A2 | 10/2002 | | |
| WO | WO 02/085402 A | 10/2002 | | |
| WO | WO 03015748 A2 * | 2/2003 | | |
| WO | WO 2005/102271 A2 | 11/2005 | | |
| WO | WO 2005/102271 A3 | 11/2005 | | |

OTHER PUBLICATIONS

Definition of 'unit dose' provided by the Oregon Legislature and found at OregonLaws.org: "'Unit dose' means a sealed single-unit container so designed that the contents are administered to the patient as a single dose, direct from the container" (from the website http://www.oregonlaws.org/glossary/definition/ unit_dose; downloaded May 18, 2014.*

Roberta Cavalli, Elena Peira, Otto Caputo, Maria Rosa Gasco. Solid lipid nanoparticles as carriers of hydrocortisone and progesterone complexes with b-cyclodextrins. International Journal of Pharmaceutics 182 (1999) 59-69.*

Naoki Inagaki and Hiroichi Nagai. Drugs for the Treatment of Allergic Diseases. Jpn. J. Pharmacol. 86, 275-280 (2001).*

Ann J-S et al., Release of triamcinolone acetonide from mucoadhesive polymer composed of chitosan and poly (acrylic acid) in vitro, Biomaterials, Elsevier Science Publishers BV, Mar. 15, 2002, pp. 1411-1416, vol. 23, No. 6, GB.

Nakamura K et al., Uptake and release of budesonide from mucoadhesive, pH-sensitive copolymers and their applicaiton to nasal delivery, Journal of Controlled Release, Sep. 20, 1999, vol. 61, No. 3, Elsevier, Amsterdam, NL.

Martindale—The complete drug reference, Pharmaceutical Press, 2000, p. 1010-1017, vol. 242330 XP002373045, Issue 242330 XP002373045.

Quintero, et al.; "A More Rapid Route of Administration of Corticosteroids in Bronchial Asthma"; The Allergy Division, West Virginia University Medical School, Morgantown, West Virginia; supported by Schering Corporation grant to the West Virginia University Foundation, Inc.; vol. 26, Sep. 1968.

Shin et al.; "Enhanced bioavailability by buccal administration of triamcinolone acetonide from the bioadhesive gels in rabbits"; International Journal of Pharmaceutics; 209 (2209) 37-43; accepted Aug. 2, 2000.

Rassing; "Chewing gum as a drug delivery system"; Advanced Drug Delivery Reviews, 13 (1994) 89-12; Department of Pharmaceutics, The Royal Danish School of Pharmacy, Copenhagen, Denmark.

Ceschel, et al; "Design and Evaluation of Buccal Adhesive Hydrocortisone Acetate (HCA) Tablets"; Drug Delivery 8:161-171, 2003.

Mumtaz, et al.; "Design of a dissolution apparatus suitable for in situ release study of tramcinolone acetonide from bioadhesive buccal tablets"; International Journal of Pharmaceutics 121 (1995) 129-139.

Parfitt, Kathleen; Corticosteroids; Martindale—The complete drug reference ($32^{nd}$ edition); 1999; pp. 1010-1017; Pharmaceutical Press; London, UK.

* cited by examiner

PHARMACEUTICAL COMPOSITIONS FOR ACUTE GLUCOCORTICOID THERAPY

FIELD OF THE INVENTION

The present invention relates to glucocorticoid-containing pharmaceutical compositions or kits for use in acute emergency situations where acute glucocorticoid therapy is required. Notably, the invention relates to pharmaceutical compositions and kits that are designed to be administered by non-medically trained persons outside a hospital or another medical or clinical setting. The invention also relates to a method for treating a disorder requiring acute glucocorticoid therapy by providing a fast onset of action of a glucocorticoid.

BACKGROUND OF THE INVENTION

Glucocorticoids are important steroids for intermediary metabolism, immune function, musculoskeletal and connective tissue as well as the brain. The importance of the glucocorticoids is best understood in patients with glucocorticoid deficiency. In such patients, the one-year survival rate was only 20% in the 1950s before the availability of glucocorticoid replacement therapy. The major use of glucocorticoids in clinical practice began, however, with their use in the treatment of rheumatoid arthritis in the 1940s. Both natural and synthetic glucocorticoids have been employed in the management of a wide variety of conditions and they play a crucial part of many emergency treatments involving allergic and inflammatory disorders.

The endogenous glucocorticoids are steroids predominantly produced in the adrenal cortex. The main glucocorticoid in the body is cortisol. The production and secretion of cortisol is governed by a complex and highly efficient system that includes the hypothalamus, pituitary and the adrenal glands i.e. hypothalamic-pituitary-adrenal axis (HPA). Cortisol secretion has a circadian release rhythm with peak values in early morning and trough values at midnight. The HPA axis is also activated by several physical and psychological stressors. Thus, under stress conditions, such as physical activity, fever, surgery or mental stress, the serum cortisol concentration is increased.

Adrenocortical deficiency results in a number of complex symptoms that results from deficiency of adrenocortical hormone activity. It may be of a primary type as a result of a disease in the adrenal cortex, a secondary (central) type due to the specific pathology in the hypothalamus and/or the pituitary gland, or a tertiary type due to a suppressed HPA axis after long-term high dose glucocorticoid treatment.

The onset of adrenocortical insufficiency may vary from insidious to an acute life-threatening situation with severe salt and water deficit, which leads to shock and death if not treated fast and adequately.

Therapy of e.g. acute adrenal crisis requires that the one or more glucocorticoids quickly enter (are absorbed) into the systemic circulation at a therapeutically effective concentration interval (therapeutic window). Although a number of various glucocorticoid-containing pharmaceutical compositions already are on the market, most of these are not suitable for the treatment of a disorder requiring acute glucocorticoid therapy as they either result in a too slow appearance in the systemic circulation (e.g. conventional tablets) or in a too low, if any, glucocorticoid serum level (many glucocorticoid-containing pharmaceutical compositions are intended for local treatment e.g. in the nose or on the skin).

There are today two ways of administering glucocorticoids in medical emergencies. One is the parenteral route where an intravenous (IV) infusion has to be set up or a deep intramuscular (IM) injection has to be given. However, one disadvantage of this administration is that an IV route can be challenging to establish particularly in patients with compromised peripheral circulation. Furthermore, parenteral administration requires qualified personnel and is therefore limited to well-crewed ambulances and in-hospital settings.

The other administration route is traditionally by oral administration using a dissolvable betamethasone tablet in water. This route is mainly used in outpatient clinics and for patient self-medication. However, the disadvantages are the considerable lag-time when preparing the solution and the time from intake until a significant serum level of the drug is obtained. The maximum plasma concentration ($C_{max}$) is usually reached within 1 to 3 hours after administration ($T_{max}$) It is also well known that the onset of intestinal absorption cannot be earlier than 0.5 hour for these oral immediate release products of a rapidly dissolved and rapidly absorbed drug (a class I drug according to the FDA's Biopharmaceutics Classification System), the gastric emptying being very variable both in the fasted and fed state. Furthermore, it is mandatory that the patient is conscious and has unaffected ability to swallow the solution since a weak gastrointestinal motility results in a further delay in gastric emptying and reduced intestinal absorption (both rate and extent).

Examples of such cumbersome oral administrations are obtained in patients with acute laryngitis, patients with severe distress due to breathlessness, children with croup or severe angioedema, and in patients with gastroenteritis where gastrointestinal absorption is uncertain.

Accordingly, it would be of great therapeutic advantage to develop pharmaceutical compositions that enable self-administration by patients and administration to patients by non-medically trained persons outside of a hospital, clinic, ambulance, paramedical or similar medical settings and at the same time result in a sufficient treatment of a disorder requiring acute glucocorticoid therapy (e.g. acute adrenal crises) by providing a fast onset of action after administration. Moreover, there is also a need for pharmaceutical compositions that can be administered to a patient who e.g. is unconscious or otherwise unable to swallow a composition (e.g. a tablet or solution) and that does not require medically trained personnel or need be done in a medical setting.

DETAILED DISCLOSURE OF THE INVENTION

The present invention meets the above-described needs by providing a pharmaceutical composition comprising one or more glucocorticoids for substantially immediate release, wherein at least about 60% of the one or more glucocorticoids are released from the composition within the first 30 min after start of an in vitro dissolution test according to USP employing USP Dissolution Apparatus No. 2 (paddle), 50 rpm and a suitable dissolution medium such as, e.g., water, simulated saliva or simulated intestinal fluid without enzymes, and wherein a glucocorticoid serum level of a subject of at least 20% of $C_{max}$ is reached within 20 min after administration of the composition via a mucosa of the subject.

The dissolution medium can be chosen depending on the type of composition in question. Accordingly, water or simulated saliva can be used for compositions intended for administration to the oral cavity. A person skilled in the art will know how to chose the right dissolution medium depending on the formulation in question. Normally a dissolution medium based on water and adjusted to a pH in the range of from pH 4.5 to about 8 is suitable irrespective of whether the compositions are intended for administration via nasal, rectal, vaginal mucosa.

In the present context the term "substantially immediate release" is intended to include all types of release which differ from the release obtained from plain tables and provide a release, which is faster than that obtained from plain tablets. In particular, the term is related to a rapid release of the one or more glucocorticoids in an in vitro dissolution test according to USP employing USP Dissolution Apparatus No. 2 (paddle), 50 rpm and simulated intestinal fluid without enzymes as dissolution medium.

The term "$C_{max}$" denotes the average maximum serum/plasma/blood concentration or serum/plasma/blood level obtained after administration of the composition to at least six normal healthy human subjects.

The term "via a mucosa" indicates that the one or more glucocorticoids must enter into the systemic circulation in order to obtain the desired effect and that the administration route is different from that of topical, intravenous and intramuscular administration.

In another aspect, the invention relates to a kit for treating a subject suffering from a disorder requiring acute glucocorticoid therapy comprising one or more containers for housing a pharmaceutical composition according to the invention and instructions for use thereof. In a specific embodiment, the one or more containers are in the form of blisters or blister packs.

In a further aspect, the invention relates to a method for treating a subject suffering from a disorder requiring acute glucocorticoid therapy, the method comprises administering via a mucosa of the subject an effective amount of one or more glucocorticoids to obtain a fast rise in the glucocorticoid serum level to at least 20% of $C_{max}$ within 20 min after administration.

In a still further aspect, the invention relates to the use of an amount of one or more glucocorticoids for the preparation of a pharmaceutical composition or kit as defined herein for the treatment of a disorder requiring acute glucocorticoid therapy by providing a fast rise in the glucocorticoid serum level to at least 20% of $C_{max}$ within 20 min after administration via a mucosa.

As mentioned above, in order to obtain a fast onset of action it is required that a fast rise of glucocorticoid serum level is obtained after administration of a composition of the invention. Accordingly, in specific embodiments least 40% of $C_{max}$ is reached within 30 min and/or at least 75% of $C_{max}$ is reached within 45 min after administration of the composition via a mucosa of the subject.

Normally, $T_{max}$ (i.e. the time it takes to obtain the maximum serum/plasma/blood concentration in the serum/plasma/blood concentration time profile) is reached within 60 min after administration of the composition via a mucosa of the subject. $T_{max}$ is typically within a range of from about 30 to about 75 min such as in a range of from about 45 to about 60 min.

As mentioned above, the pharmaceutical compositions and kits of the present invention are suitable for use in the treatment of a disorder requiring acute glucocorticoid therapy. Examples of such disorders are acute adrenal crises relating to a primary, secondary or tertiary adrenal insufficiency, an anaphylactic reaction, an Addison crisis, a status asthmaticus, a blood transfusion reaction, a brain edema, acute kidney transplant rejection, systemic lupus erythematosus or a severe allergic reaction. Other examples include inflammatory disorders, autoimmune disorders, or medical disorders in which a glucocorticoid forms a part of the first line emergency medical treatment or intense short-time medical treatment. Specific examples of disorders that can be treated according to the present invention are given in the following.

Active Substance, Dosage and Administration Routes

In the present context, the term "glucocorticoid" or "glucocorticosteroid" is intended to denote a therapeutically, prophylactically and/or diagnostically active glucocorticoid or a glucocorticoid that has physiologic effect. The term is intended to include the glucocorticoid in any suitable form such as e.g. a pharmaceutically acceptable salt, complex, solvate, ester, active metabolites or prodrug thereof of in any physical form such as, e.g., in the form of crystals, amorphous or a polymorphous form or, if relevant, in any stereoisomer form including any enantiomeric or racemic form, or a combination of any of the above. The glucocorticoid may be a synthetic glucocorticoid.

The one or more glucocorticoids used according to the invention are selected from the group consisting of hydrocortisone, cortisone, prednisolone, prednisone, methylprednisone, triamcinolone, paramethasone, betamethasone, dexamethasone and fludrocortisone including pharmaceutically acceptable esters, salts, complexes and mixtures thereof. In a preferred embodiment of the invention, the glucocorticoid is betamethasone.

Specific examples of pharmaceutically acceptable salt suitable for use according to the invention are phosphates, succinates, lysinates, acetates, cypionates, valerates, hemisuccinates, butyrates and trometamole salts.

As the glucocorticoid is intended for immediate release, the release and/or absorption into the systemic circulation takes place already in the oral cavity in the case the composition is administered orally. In such cases, the glucocorticoid of choice for the first part may be any other than hydrocortisone (as such) or cortisone as these two active substances have a bitter taste. However, these substances may be employed provided that a sufficient taste masking is obtained. In the paragraph relating to "Pharmaceutically acceptable excipients" taste-masking is discussed in more detail. Accordingly, the one or more glucocorticoids of the first part may have an acceptable taste, may be tasteless or it may be effectively taste-masked.

Furthermore, in specific embodiments of the invention, the glucocorticoid used may be a readily water-soluble glucocorticoid (e.g. a water-soluble salt of the glucocorticoid) in order to ensure a fast dissolution of the glucocorticoid from the composition.

In a preferred embodiment of the invention the glucocorticoid is hydrocortisone trometamole (or succinate) due to its high solubility in water, which in turn leads to a rapid absorption into the systemic circulation.

Dosage

In general, the dosage of the glucocorticoids present in a composition according to the invention depends inter alia on the specific drug substance, the age and condition of the patient and of the disease to be treated.

The term "hydrocortisone equivalents" is used herein to define the amount in mg of a specific glucocorticoid that corresponds to 1 mg of hydrocortisone for the purpose of glucocorticoid therapy as generally understood by medical practitioners. The term is based on the fact that the individual glucocorticoids have different potency and in order to achieve a desired therapeutic effect different doses of the individual glucocorticoids are required. Equivalent doses of the glucocorticoids can be calculated based on the following table.

| Glucocorticoid | Equivalent amount (mg) | Hydrocortisone equivalent (1 mg of the glucocorticoid corresponds to the listed amount in mg of hydrocortisone) |
| --- | --- | --- |
| Cortisone acetate | 25 | 0.8 |
| Hydrocortisone | 20 | 1 |
| Prednisolone | 5 | 4 |
| Prednisone | 5 | 4 |
| Methylprednisolone | 4 | 5 |
| Triamcinolone | 4 | 5 |
| Paramethasone | 2 | 10 |
| Betamethasone | 0.75 | 26.66 |
| Dexamethasone | 0.75 | 26.66 |
| Fludrocortisone | 0.05 | 400 |

In general, a pharmaceutical composition according to the invention contains a total amount of the one or more glucocorticoids expressed as hydrocortisone of from about 1 to about 200 mg. In specific embodiments, the total amount of the one or more glucocorticoids expressed as hydrocortisone is from about 1 to about 175 mg such as, e.g., from about 1 to about 150 mg, from about 1 to about 100, from about 1 to about 75 mg, from about 1 to about 70 mg, from about 1 to about 60 mg, from about 5 to about 50 mg, from about 5 to about 40 mg or from about 10 to about 30 mg.

More specifically, normal dose ranges are given below for acute glucocorticoid therapy

| | |
| --- | --- |
| Hydrocortisone | 1-200 mg; in acute adrenal crises about 100 mg |
| Cortisone | 1-200 mg such as about 100 mg |
| Betamethasone | 1-20 mg; in increased intracranial pressure e.g. brain oedema about 4 mg daily<br>In chemotherapy or radiation induced nausea 4-8 mg |
| Prednisolon | 1-100 mg; such as from 1 to 30 mg daily; in severe cases 50-60 mg/day |
| Dexamethasone | 0.1-6 mg such as 0.5-2 mg or 1.5-3 mg; in severe cases up to 6 mg/day |
| Fludrocortisone | 0.05-5 mg; in Addison disease to correct inadequate electrolyte balance 0-05-0.2 mg daily;<br>Cortical adrenal hyperplasia ("salt losing adrenogental syndrome") 0.1-0.2 mg |
| Prednisone | 10-100 mg such as 50 mg |
| Methylprednisolone | 2-40 mg such as 2-20 mg |

In the following are given suitable doses of the individual glucocorticoids in various treatment regimens.

| Acute asthma - adults | |
| --- | --- |
| betamethasone | 4-8 mg |
| prednisolone | 30-60 mg |
| methylprednisolone | 40 mg |
| Acute anaphylaxia - adults | |
| betamethasone | 5 mg up to 20 mg |
| hydrocortisone | 200 mg |
| dexamethasone | 4-20 mg-80 mg |
| Acute anaphylaxia - children | |
| hydrocortisone | 100-200 mg |

| Septic shock - adults | |
| --- | --- |
| hydrocortisone | 200-300 mg/day |
| methylprednisone | 30 mg/kg |
| Acute bacterial meningitis | |
| dexamethasone | 0.3 mg/kg/dose (max 10 mg) × 4 times daily for 2-4 days |
| betamethasone | 8 mg × 4 times daily |
| Acute RSV (respiratory syncytial virus) infection with bronchiolitis in children | |
| betamethasone | 4-6 mg |
| Acute croup - children | |
| betamethasone | 4-6 mg |
| Mononucleosis with complications (airway obstruction, thrombocytopenia or haemolytical anaemia) | |
| betamethasone | 5-6 mg |
| Tonsillitis/peritonsillitis - children with airway obstruction | |
| betamethasone | 4-6 mg |

A composition according to the invention is designed to provide a fast onset of action and upon administration a fast rise in glucocorticoid serum/plasma/blood level is obtained. In the case hydrocortisone is used as the glucocorticoid a serum level of at least about 200 nmol/l is obtained within 20 min after administration. In the case that another glucocorticoid than hydrocortisone is used, a person skilled in the art will know how to determine suitable equivalent serum/plasma/blood concentrations.

For example, hydrocortisone can be rapidly released from a composition during a time period of from about 0 to abut 30 minutes after administration and 5-10 mg of hydrocortisone can be rapidly administered as an extra dose in conjunction with fever etc in patients with adrenal insufficiency. Likewise, 5-20 mg of betamethasone can be rapidly released for most indications in which a rapid glucocorticoid effect is of value.

Administration Routes

As mentioned above, the one or more glucocorticoids used according to the invention are administered to the subject (preferably a human) via a mucosa into the systemic circulation. In particular, in specific embodiments of the invention, the mucosa is the mucosa in the oral cavity, the nose, the rectum or in the vagina or via pulmonary, bronchial or respiratory mucosa and epithelia. Preferably, the mucosa is the oral mucosa.

FIGS. 11 and 12 show sites of oral mucosal administration suitable for use. Four well-defined sites may be used, namely "buccal" administration that includes the term "labial" administration and is used for administration of a pharmaceutical composition to a mucosa between the gums (gingiva) and the inside of the cheeks;

"sublingual" administration that refers to administration of a pharmaceutical composition under the tongue;

"palatal" administration that refers to administration of a pharmaceutical composition to the hard and/or soft palate; and "gingival" administration that refers to administration of a pharmaceutical composition to the upper and/or lower gingiva.

All the above-mentioned sites are suitable for use to obtain a very fast onset of action due to a rapid absorption (transport of active drug) into the systemic circulation. In specific embodiments of the invention the buccal administration route is preferred, i.e. administration of a composition to the oral mucosa between the gums and the inside of the cheeks and thus enabling the absorption to take place from two sites, namely the gingival mucosa and the buccal mucosa.

Pharmaceutical Compositions

In the following is given a description of pharmaceutical compositions according to the invention.

Release of the One or More Glucocorticoids

A rapid release of the one or more glucocorticoids is necessary in order to obtain a fast onset of action after administration via a mucosa where the glucocorticoid is rapidly absorbed (transported) into the systemic circulation. Accordingly a general requirement is that at least 60% of the one or more glucocorticoids contained in the composition must be released within 30 min when tested in an in vitro dissolution test as defined herein. Specific embodiments of the composition fulfil one or more of the requirements given in the following table. In general, it is preferred that the requirement stated within 30 min after start of the dissolution test is fulfilled. In preferred embodiments, at least 70% or at least 80% of the one or more glucocorticoids contained in the composition are released within the first 20 min of the dissolution test.

| time after start of the dissolution test | % hydrocortisone equivalents released (based on the content in the composition) |
| --- | --- |
| within 30 min | at least about 60% such as, e.g., at least about 70%, preferably at least about 80% or more preferably at least about 90% |
| within 20 min | at least about 60%, preferably at least about 70%, at least about 80% or even more preferred at least about 90% |
| within 15 min | at least about 60% such as, e.g., at least about 70%, preferably at least about 80% or at least about 90% |
| within 10 min | at least about 60% such as, e.g., at least about 70%, preferably at least about 80% or at least about 90% |
| within 5 min | at least about 60% |

In specific embodiments (cf. the examples herein) more than 50% of the one or more glucocorticoids can be released within 2 min, between 50 and 90% can be released within 5-8 min, and more than 90% of the dose can be released within 15 min.

A pharmaceutical composition according to the invention is designed for systemic administration via a mucosa. In a preferred embodiment the mucosa is the mucosa in the oral cavity.

The pharmaceutical composition may be in any suitable form including liquid, semi-solid or solid form.

In a preferred aspect of the invention the pharmaceutical composition is in the form of a dosage form such as a unit dosage form.

Examples of compositions according to the invention suitable for administration via the oral mucosa into the systemic circulation are typically solid or semi-solid dosage forms. The solid dosage form is typically selected from the group consisting of granules, beads, pellets and powders and—when presented in unit dosage form—it may be in the form of a tablet including a chewable tablet, a suckable tablet, an effervescent tablet, a sublingual tablet, a rapid-burst tablet, an immediate release tablet, a rapidly dissolvable tablet, melt tablets, lozenges, pastilles or it may be presented in a more candy-like form, or the like.

A pharmaceutical composition for administration via the oral mucosa into the systemic circulation may also be in the form of a spray, a wafer, a film, a gel, a hydrogel, a patch, a gingival patch, a bioadhesive patch, a sachet, a solution, an inhaler or the like.

Examples of compositions according to the invention suitable for administration via the mucosa in the nose into the systemic circulation are typically in the form of nasal sprays, nasal aerosols, nasal solutions including nasal drops and the like.

Examples of compositions according to the invention suitable for administration via the pulmonary, bronchial and respiratory mucosa and epithelia into the systemic circulation are inhalers including powder inhalers.

Examples of compositions according to the invention suitable for administration via the mucosa in the rectum or the vagina into the systemic circulation include suppositories, vagitories, clysmas etc.

A pharmaceutical composition according to the invention may also have bio/mucoadhesive properties. The absorption of drugs into the systemic circulation from a mucosal drug delivery system is significantly improved if a mucosal bioadhesive component is added in the formulation. It will prevent both swallowing and create a high local concentration of the glucocorticoid adjacent to the absorption site. The mucoadhesive component will be mixed in an appropriate way together with the glucocorticoid and other ingredients in the dosage form. The term "bio/mucoadhesive is used to denote that the composition is able to reversible adhere to a biological mucosa. In some cases a bio/mucoadhesion promoting agent is included in the composition to promote adherence to the mucosa.

In the term bio/mucoadhesion promoting agent mucoadhesion and bioadhesion are used interchangeable even if bioadhesion may have a wider definition meaning that an adhesion to any biological feature available at the mucosa takes place. If present, the bio/mucoadhesion promoting agent may be a polymeric substance, preferable a substance having an average molecular weight above 5 kD. The hydration property is crucial for the bio/mucoadhesion forces and therefore a rapid swelling of the polymer will initiate the bio/mucoadhesion process. A swelling factor by volume when brought into contact with the saliva fluid should be between 10 and 20.

A pharmaceutical composition according to the invention typically contains one or more pharmaceutically acceptable excipients. A general description of pharmaceutically acceptable excipients suitable for use in a composition according to the present invention is given in the paragraph under the heading "Pharmaceutically acceptable excipients". Depending on the specific kind of dosage form a person skilled in the art will know which kinds of excipients to choose, if necessary guided by the teaching in handbooks like Remington's Pharmaceutical Science and Handbook of Pharmaceutical Excipients. In the following is given a description of specific kinds of excipients suitable for use in the formulation of compositions in the form of film or patches especially for administration to the oral cavity.

When the pharmaceutical composition is in the form of a film, patch, wafer, gel, sachet, gingival patch or the like it may contain a pharmaceutically acceptable excipient selected from the group consisting of an acrylic polymer including a derivative thereof, a cellulose derivative, modified starch, polyethylene oxide, chitosan, gelatin, sodium alginate, pectin, scleroglucan, xanthan gum, guar gum, or poly-co-(methyl vinyl ether-maleic anhydride), alone or in combinations thereof. The cellulose derivative may be selected from the group consisting of hydroxypropylmethyl cellulose, hydroxyethyl cellulose, hydroxypropyl cellulose, sodium carboxymethyl cellulose, methyl cellulose, ethyl hydroxyethyl cellulose, carboxymethyl cellulose, microcrystalline cellulose, modified cellulose gum, or crosscaramellose.

A pharmaceutical composition according to the invention may also contain the one or more bio/mucoadhesion promoting agents. Normally such bio/mucoadhesion promoting agents are present in concentration of from about 0.1 to about 25% w/w. Examples of bio/mucoadhesion promoting agents include polymers including synthetic polymers, natural polymers and derivatives thereof, and mixtures thereof. The polymer may be selected from a carbomer, a polyethylene oxide, a poly co-(methylvinyl ether/maleic anhydride, and mixtures thereof; or it may be a polysaccharide. The polysaccharide may be selected from the group consisting of gelatin, sodium alginate, pectin, scleroglucan, xanthan gum; guar gum, microcrystalline cellulose, crosscaramellose, hydroxypropyl cellulose, methyl cellulose, ethyl cellulose, hydroxyethyl cellulose, hydroxypropyl cellulose, ethyl hydroxyethyl cellulose, carboxymethyl cellulose, sodium carboxymethyl cellulose, moderately cross-linked starch, and chitosan.

A pharmaceutical composition according to the invention may also containing a dissolution promoting agent. If present, a dissolution promoting agent is present in a concentration of from about 0.05 to about 5% w/w of the total weight of the composition. The dissolution promoting agent may be selected from the group consisting of sodium lauryl sulphate, a polysorbate, a bile acid, a bile salt, a salt of cholic acid or cholanic acid, isopropyl myristate, methyl laurate, oleic acid, oleyl alcohol, glycerol monoleate, glycerol dioleate, glycerol trioleate, glycerol monostearate, glycerol monolaurate, propylene glycol monolaurate, sodium dodecyl sulfate, and a sorbitan ester.

In specific embodiment the one or more glucocorticoids in a composition of the invention are present as microparticles or nanoparticles. In general, he mean particle size of such particles is 10 µm or less. Furthermore, the micro- or nanoparticles may be encapsulated such as coated with a coating comprising a lechitin or a lechitin based compound.

When the glucocorticoid is present in the form of micro- or nanoparticles, a pharmaceutical composition according to the invention may also comprise a disintegrating agent. Such agents promote the dispersion of microparticles of the glucocorticoid over the administration site in for example the labial and gingival mucosa. Examples of pharmaceutically acceptable disintegrating agents are cross-linked polyvinylpyrrolidone, carboxymethyl starch, natural starch, microcrystalline cellulose, and cellulose gum. If present, it is normally used in a concentration of from 0.5 to 10 w/w based on the total weigh of the composition Different pharmaceutical excipients, such as mannitol and lactose, have been found to be particularly suitable as excipients.

As mentioned above, the pharmaceutical composition according to the invention may further comprise a taste-masking agent. Examples of a taste-masking agent are e.g. menthol, peppermint, vanillin, a terpene based compound, or an artificial sweetener. In a specific embodiment, the one or more glucocorticoids are taste masked by incorporation into an inclusion complex by means of alpha-, beta-, or gamma-cyclodextrins, preferably by beta-cyclodextrins.

In general, the composition of the invention contains from 0.05 up to 50 weight percent such as, e.g., from 0.05 up to 40 weight percent, 0.05 up to 30 weight percent or from about 0.05 up to 20 weight percent of glucocorticoid. More preferably, the compositions contains from 0.05 to 10 weight percent of glucocorticoid, and especially from 0.1 to 5 weight percent. The contents can also be expressed as the amount of glucocorticoid in a dose unit of the composition, such as a tablet. In this connection a dose refers to the therapeutically amount of the at least one glucocorticoid, or its derivative, which is to be administered at one time. When the glucocorticoid is used in the form of a pharmaceutically acceptable salt, these percentages and amounts should be recalculated accordingly.

Pharmaceutically Acceptable Excipients

In the present context the terms "pharmaceutically acceptable excipients" are intended to denote any material, which is inert in the sense that it substantially does not have any therapeutic and/or prophylactic effect per se. Such an excipient may be added with the purpose of making it possible to obtain a pharmaceutical, which have acceptable technical properties.

Examples of suitable excipients for use in a solid dosage form according to the invention include fillers, diluents, disintegrants, binders, lubricants etc. or mixture thereof. As the individual parts of a composition or kit according to the invention are used for different purposes (e.g. immediate and extended release), the choice of excipients is normally made taken such different uses into considerations. A person skilled in the art will know which kinds of pharmaceutically acceptable excipients that are suitable choices depending on the specific dosage form in question. Other pharmaceutically acceptable excipients for suitable use are e.g. acidifying agents, alkalising agents, preservatives, antioxidants, buffering agents, chelating agents, colouring agents, complexing agents, emulsifying and/or solubilizing agents, flavours and perfumes, humectants, sweetening agents, wetting agents etc.

Examples of suitable fillers, diluents and/or binders include lactose (e.g. spray-dried lactose, α-lactose, β-lactose, Tabletose®, various grades of Pharmatose®, Microtose® or Fast-Floc®), microcrystalline cellulose (various grades of Avicel®, Elcema®, Vivacel®, Ming Tai® or Solka-Floc®), hydroxypropylcellulose, L-hydroxypropylcellulose (low substituted), hydroxypropyl methylcellulose (HPMC) (e.g. Methocel E, F and K, Metolose SH of Shin-Etsu, Ltd, such as, e.g. the 4,000 cps grades of Methocel E and Metolose 60 SH, the 4,000 cps grades of Methocel F and Metolose 65 SH, the 4,000, 15,000 and 100,000 cps grades of Methocel K; and the 4,000, 15,000, 39,000 and 100,000 grades of Metolose 90 SH), methylcellulose polymers (such as, e.g., Methocel A, Methocel A4C, Methocel A15C, Methocel A4M), hydroxyethylcellulose, sodium carboxymethylcellulose, carboxymethylene, carboxymethylhydroxyethylcellulose and other cellulose derivatives, sucrose, agarose, sorbitol, mannitol, dextrins, maltodextrins, starches or modified starches (including potato starch, maize starch and rice starch), calcium phosphate (e.g. basic calcium phosphate, calcium hydrogen phosphate, dicalcium phosphate hydrate), calcium sulfate, calcium carbonate, sodium alginate, collagen etc.

Specific examples of diluents are e.g. calcium carbonate, dibasic calcium phosphate, tribasic calcium phosphate, calcium sulfate, microcrystalline cellulose, powdered cellulose, dextrans, dextrin, dextrose, fructose, kaolin, lactose, mannitol, sorbitol, starch, pregelatinized starch, sucrose, sugar etc.

Specific examples of disintegrants are e.g. alginic acid or alginates, microcrystalline cellulose, hydroxypropyl cellulose and other cellulose derivatives, croscarmellose sodium, crospovidone, polacrillin potassium, sodium starch glycolate, starch, pregelatinized starch, carboxymethyl starch (e.g. Primogel® and Explotab®) etc.

Specific examples of binders are e.g. acacia, alginic acid, agar, calcium carrageenan, sodium carboxymethylcellulose, microcrystalline cellulose, dextrin, ethylcellulose, gelatin, liquid glucose, guar gum, hydroxypropyl methylcellulose, methylcellulose, pectin, PEG, povidone, pregelatinized starch etc.

Glidants and lubricants may also be included in the composition. Examples include stearic acid, magnesium stearate, calcium stearate or other metallic stearate, talc, waxes and glycerides, light mineral oil, PEG, glyceryl behenate, colloidal silica, hydrogenated vegetable oils, corn starch, sodium stearyl fumarate, polyethylene glycols, alkyl sulfates, sodium benzoate, sodium acetate etc.

Other excipients which may be included in a composition of the invention are e.g. flavoring agents, coloring agents, taste-masking agents, pH-adjusting agents, buffering agents, preservatives, stabilizing agents, anti-oxidants, wetting agents, humidity-adjusting agents, surface-active agents, suspending agents, absorption enhancing agents, agents for modified release etc.

The composition or kit components according to the invention may also be coated with a film coating, a protective coating, an anti-adhesive coating etc.

A composition according to the invention may also be coated in order to obtain suitable properties e.g. with respect to taste-masking of the one or more glucocorticoids. The coating may also be applied as a readily soluble film. The coating may be applied on single unit dosage forms (e.g. tablets) or it may be applied on a multiple-unit dosage form or on its individual units.

Suitable coating materials are e.g. methylcellulose, hydroxypropylmethylcellulose, hydroxypropylcellulose, acrylic polymers, ethylcellulose, cellulose acetate phthalate, polyvinyl acetate phthalate, hydroxypropyl methylcellulose phthalate, polyvinylalcohol, sodium carboxymethylcellulose, cellulose acetate, cellulose acetate phthalate, gelatin, methacrylic acid copolymer, polyethylene glycol, shellac, sucrose, titanium dioxide, carnauba wax, microcrystalline wax, glyceryl monostearate, zein.

Plasticizers and other ingredients may be added in the coating material. The same or different active substance may also be added in the coating material.

Taste Masking

In general, it is difficult in most cases to prepare a formulation for oral mucosa or nasal administration with satisfactory safety and stability from a drug having irritating properties or capable of forming molecular aggregates, although it depends on the kind of the drug used. In the case of hydrocortisone, the base has a distinctively bitter taste and a formulation has to be taste masked in order to be applicable for repeated use.

The taste masking agent can be a menthol, a peppermint, a vanillin, or a terpene based compound. In addition, the taste masking agent can be an artificial sweetener, e.g. sorbitol, xylitol or aspartame. Taste masking can also be achieved by microencapsulation of the glucocorticoid as particles. This is for example accomplished with lecithin based compounds. The taste masking agent is carefully mixed with the active drug in order to be present both at the surface and within the administration formulation. Taste masking can also be achieved by formation of inclusion complexes with cyclodextrins.

Typical examples of the cyclodextrin compound are alpha.-cyclodextrin, beta.-cyclodextrin, .gamma.-cyclodextrin, hydroxypropyl .beta.-cyclodextrin, dimethyl beta.-cyclodextrin, maltosyl .beta.-cyclodextrin and .beta.-cyclodextrin sulfate. Particularly preferred are .alpha.-cyclodextrin, .beta.-cyclodextrin and .gamma.-cyclodextrin. These cyclodextrin compounds may be used alone or in combination.

The amount of cyclodextrin compound to be used may vary with its solubility and the concentration of hydrocortisone. It is, however, desirable that the amount of cyclodextrin compound is 0.5 to 4.0 moles, preferably 2.0 to 4.0 moles, as much as the mole of hydrocortisone.

Method Aspect

A pharmaceutical composition or a kit according to the invention is suitable for use in the treatment of a subject such as a mammal including a human suffering from a disorder requiring acute glucocorticoid therapy.

Accordingly, in a separate aspect the invention relates to a method for treating a subject suffering from a disorder requiring acute glucocorticoid therapy, the method comprises administering via a mucosa of the subject an effective amount of one or more glucocorticoids to obtain a fast rise in the glucocorticoid serum level to at least 20% of $C_{max}$ within 20 min after administration.

Normally, it is preferred that at least 40% of $C_{max}$ is reached within 30 min after administration in order to obtain a fast onset of action. In specific preferred embodiment, at least 75% of $C_{max}$ is reached within 45 min after administration and/or $T_{max}$ is reached within 60 min after administration of the composition via a mucosa of the subject.

Details concerning other aspects of the invention are described hereinbefore and apply also to the method aspect of the invention.

The method according to the invention can be carried out by the patient itself or by non-medically trained persons due to the fact that the one or more glucocorticoids are not presented in the form of a composition for injection or infusion. Normally, medically trained personnel can only administer such compositions. Accordingly, the present invention provides a method that compared to the known treatment methods requiring acute glucocorticoids is much more simple to handle without the necessity of specialized equipment. It is therefore contemplated that the present invention provides a method that enables a treatment when the condition of the patient requires it, i.e. there is no need for bringing the patient to a hospital or a medical clinic in order to be able to give the necessary treatment.

Moreover, due to the development of compositions that enable a fast onset of action after administration and that can be administered without the need of the patient to swallow the composition (e.g. compositions of the invention in the form of films, bio/mucoadhesive compositions, patches, gingival patches, sprays etc.), the patient may be unconscious or otherwise unable to swallow normal tablets and still be correctly treated with glucocorticoids in acute situations.

Use of a Composition or a Kit According to the Invention

In another separate aspect, the invention relates to the use one or more glucocorticoids for the preparation of a pharmaceutical composition or kit as defined hereinbefore for the treatment of a disorder requiring acute glucocorticoid therapy and to provide a serum level as defined herein.

In the above is given a detailed description of the invention relating one or more aspects of the invention, in particular relating to pharmaceutical compositions. However, all details and particulars disclosed under this aspect of the invention apply mutatis mutandis to the other aspects of the invention.

LEGENDS TO FIGURES

Figure 1:
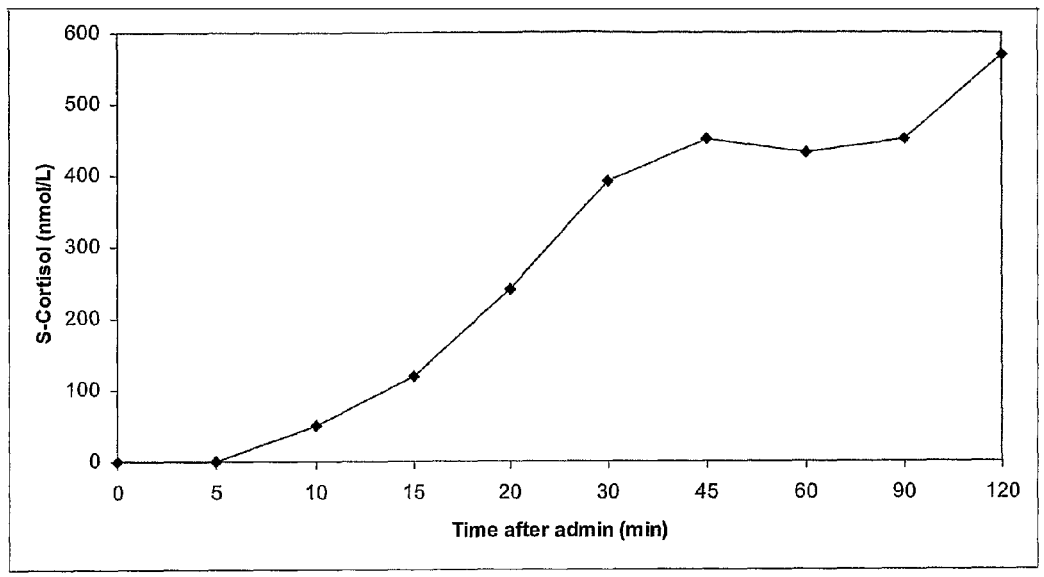
FIG. 1 shows results from Example 11. The plasma concentration-time profile of cortisol following a single dose administration of composition A to a human subject.
Figure 2:
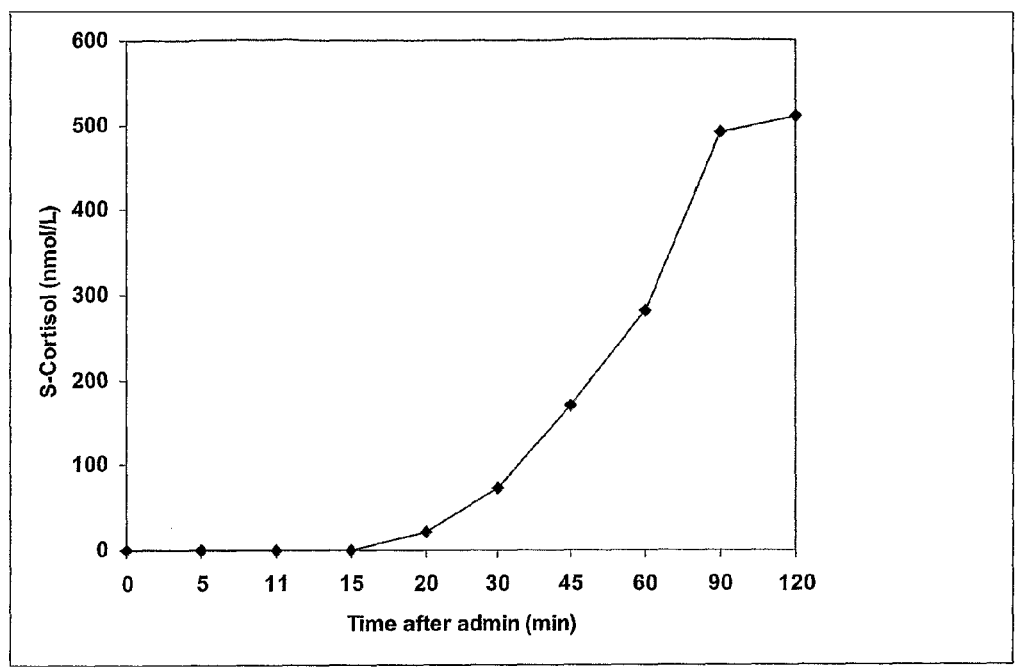
FIG. 2 shows results from Example 11. The plasma concentration-time profile of cortisol following a single dose administration of composition B to a human subject.
Figure 3:
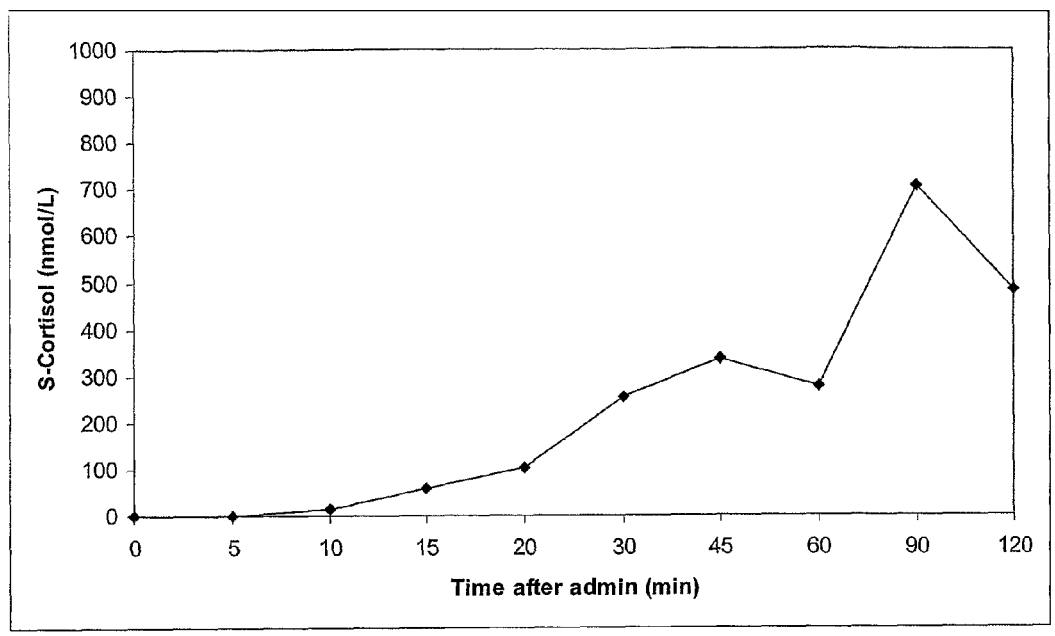
FIG. 3 shows results from Example 11. The plasma concentration-time profile of cortisol following a single dose administration of composition C to a human subject.
Figure 4:
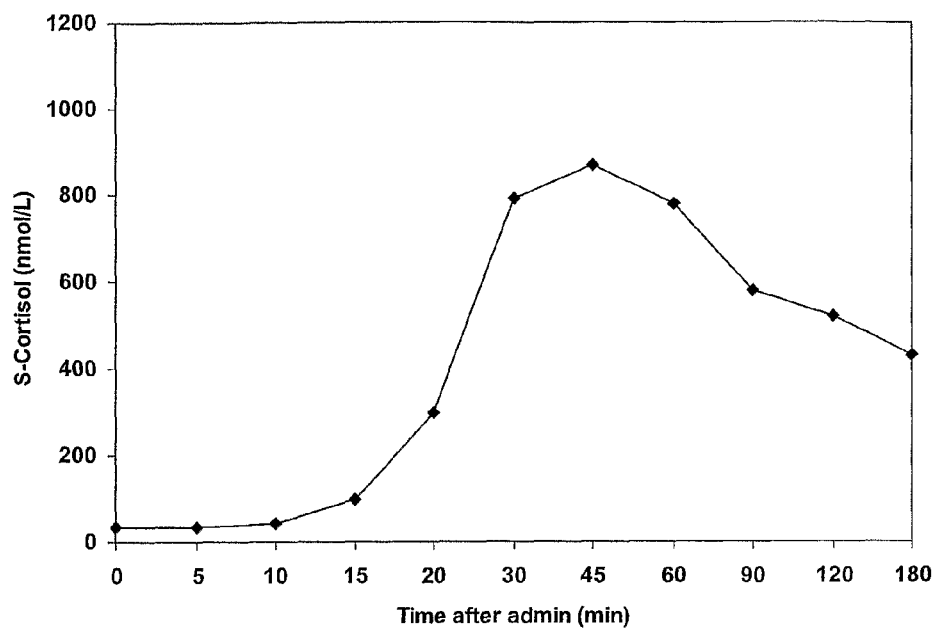

FIG. 4 shows results from Example 12. The plasma concentration-time profile of cortisol following a single dose administration of film A to a human subject. Non-mucoadhesive thin-layer film, 6 cm$^2$, 10 mg hydrocortisone, buccal administration. Subject has the endogenous glucocorticoid secretion suppressed by synthetic glucocorticoids.

Figure 5:
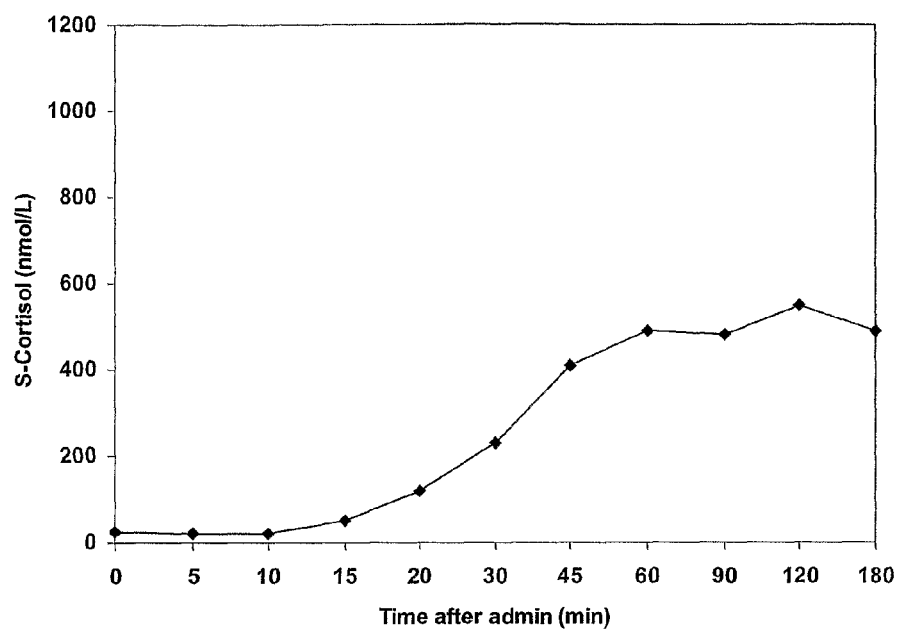

FIG. 5 shows results from Example 12. The plasma concentration-time profile of cortisol following a single dose administration of film B to a human subject. Non-mucoadhesive thin-layer film, 6 cm$^2$, 11.2 mg hydrocortisone acetate, buccal administration. Subject has the endogenous glucocorticoid secretion suppressed by synthetic glucocorticoids.

Figure 6:
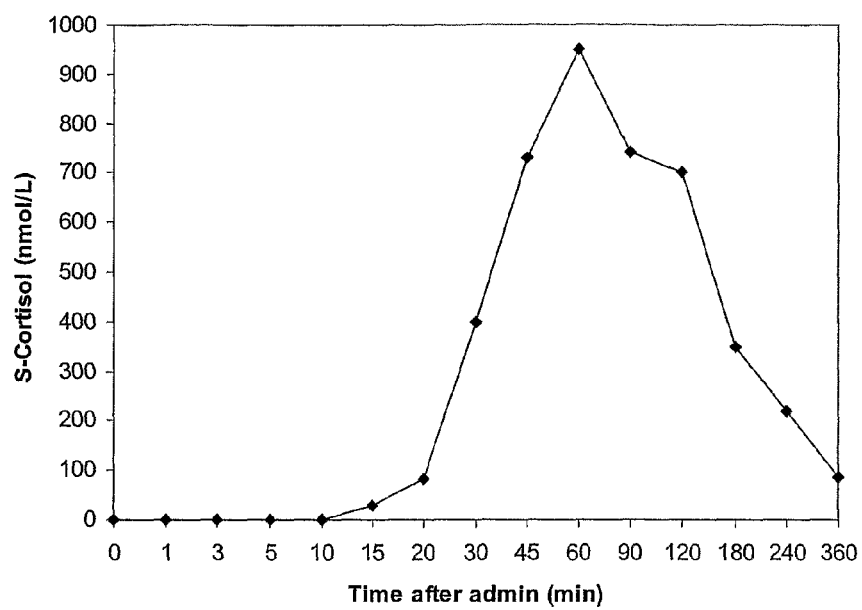
Figure 7:
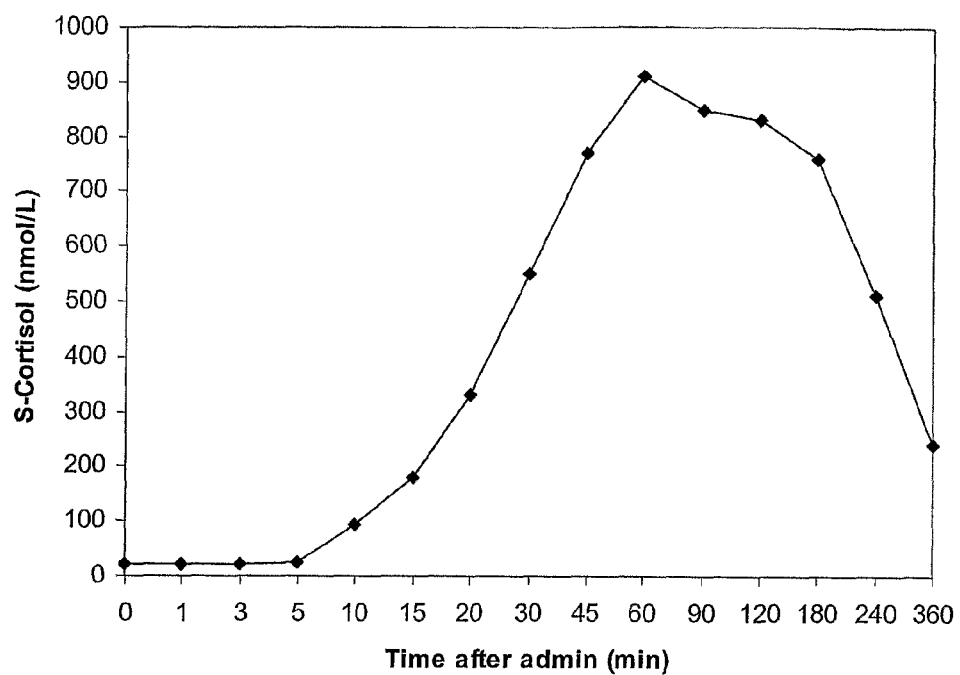
Figure 8:
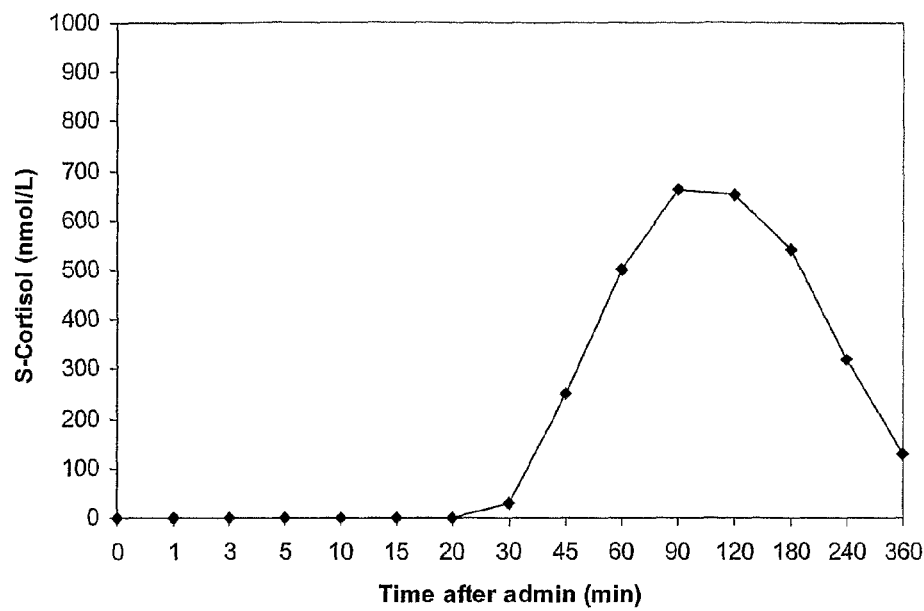
Figure 9:
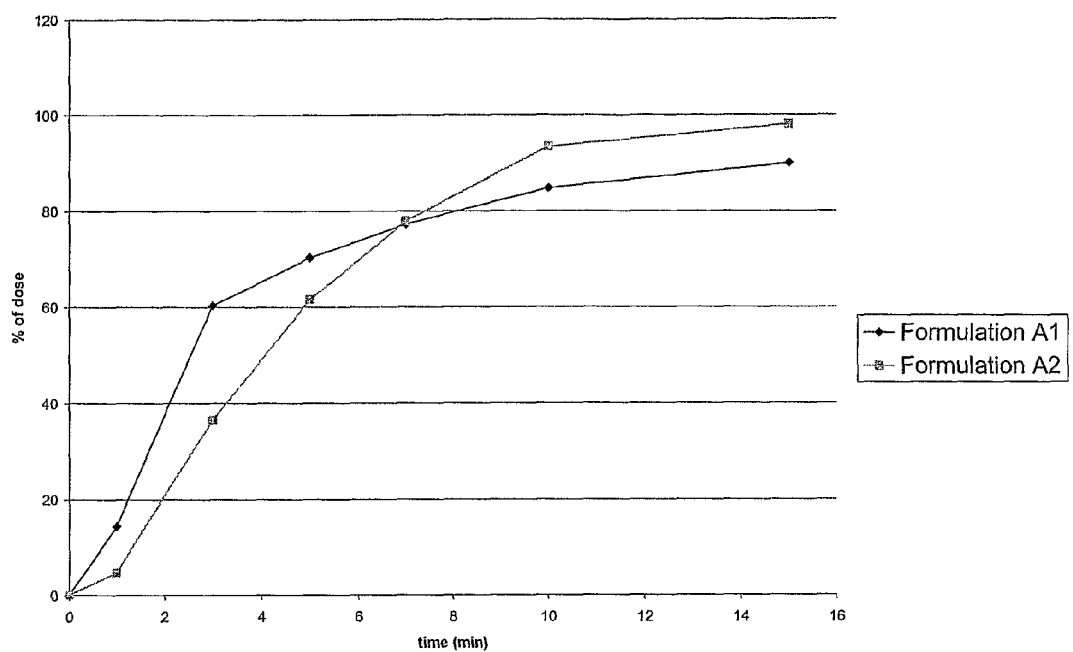

FIG. 6 shows results from Example 13. The plasma concentration-time profile of cortisol following a single dose administration of composition A to a human subject. In vivo plasma profile. Mucoadhesive thin-layer film, 10 mg hydrocortisone, buccal administration. Subject has the endogenous glucocorticoid secretion suppressed by synthetic glucocorticoids FIG. 7 shows results from Example 13. The plasma concentration-time profile of cortisol following a single dose administration of composition A to a human subject. Mucoadhesive thin-layer film, 10 mg hydrocortisone, buccal administration. Subject has the endogenous glucocorticoid secretion suppressed by synthetic glucocorticoids FIG. 8 shows results from Example 14. The plasma concentration-time profile of cortisol following a single dose administration of composition C. In vivo plasma profile. Mucoadhesive rapid-release tablet, 10 mg hydrocortisone, buccal administration. Subject has the endogenous glucocorticoid secretion suppressed by synthetic glucocorticoids FIG. 9 shows results from Example 15 (Composition C from Example 14).

Figure 10:
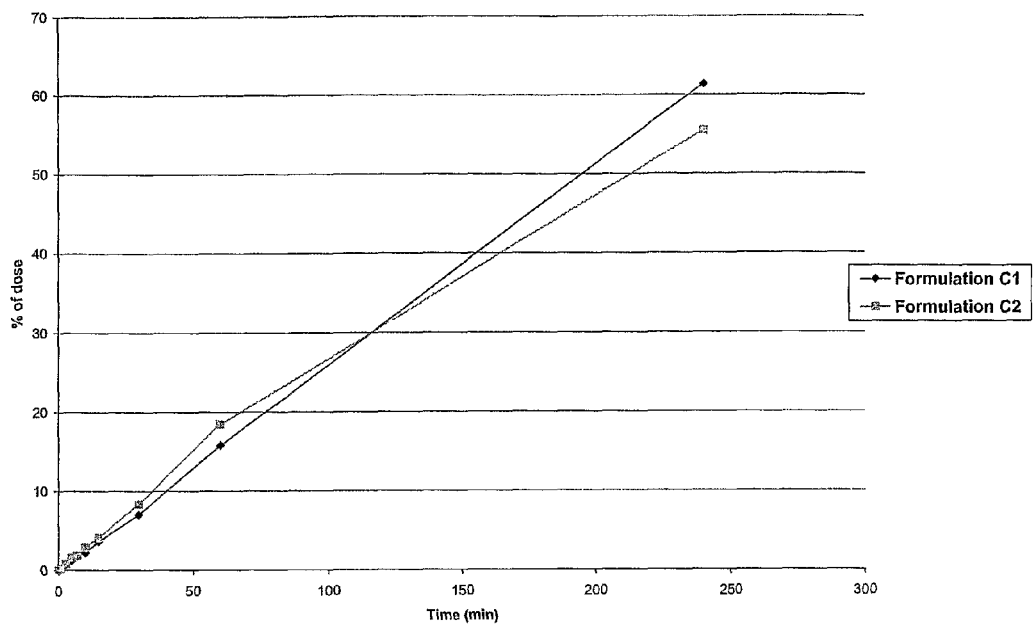

FIG. 10 shows results from Example 15 (Composition A from Example 13).

Figure 11:
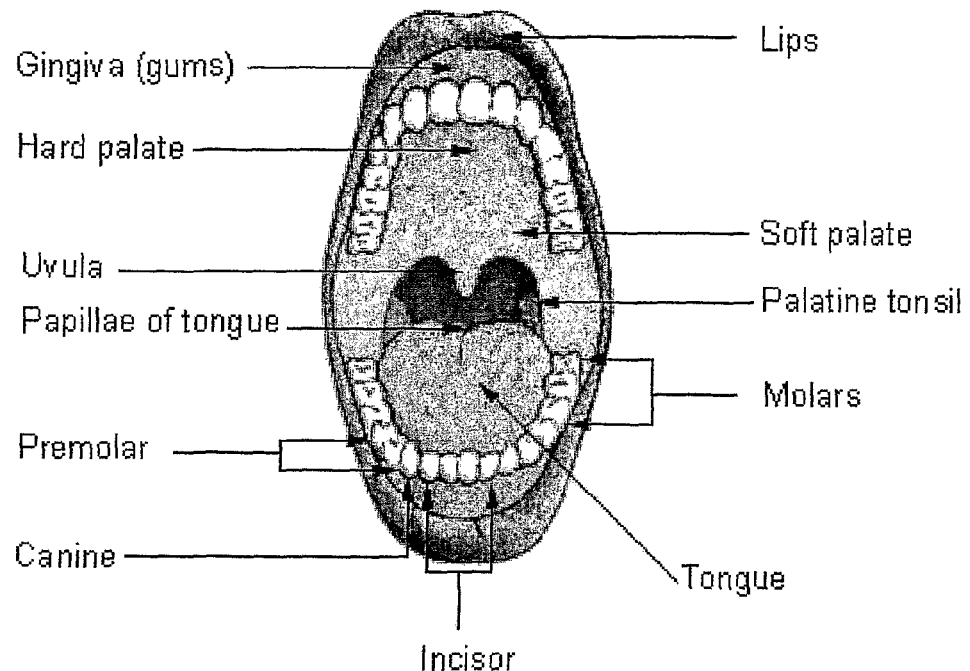
Figure 12:
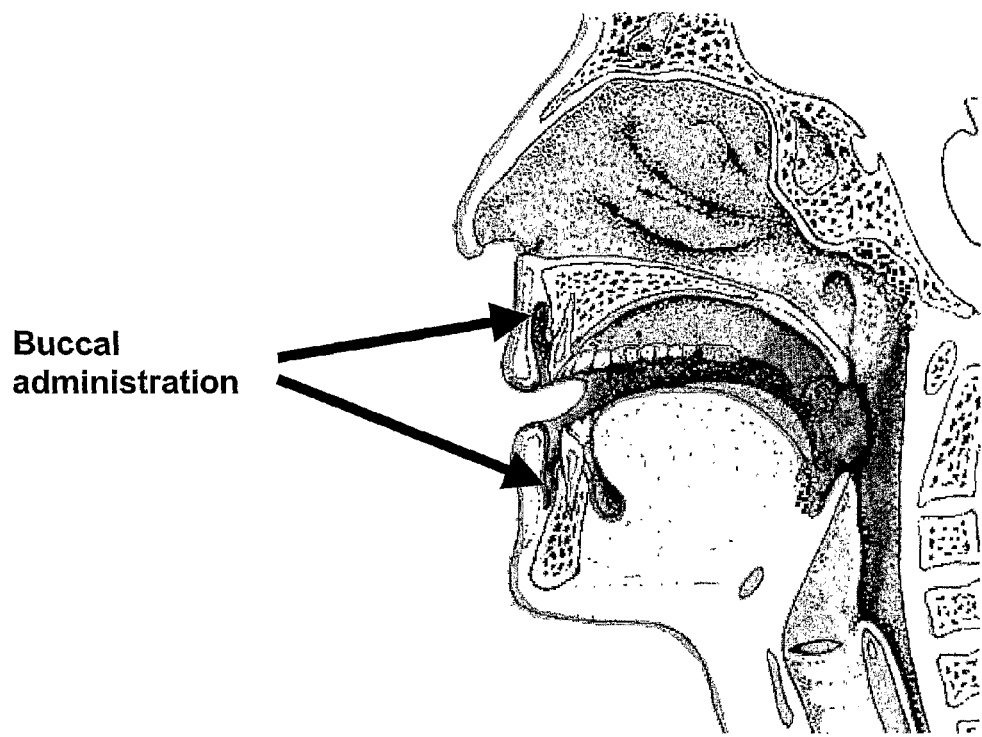

FIGS. 11 and 12 illustrates different administration sites within the oral cavity The invention is further illustrated in the following non-limiting examples.

Materials

The materials used in the following examples were

| Trade name | Chemical substance | Manufacturer |
| --- | --- | --- |
| Betamethasone | USP/NF | |
| Carboxymetylcellulose | USP/NF | |
| Chitosan glutamate | USP/NF | |
| Crospovidone | USP/NF | |
| Hydrocortisone | Ph. Eur., Qual. D | Aventis, Switzerland (by Apoteksbolaget) |
| Hydrocortisone acetate | USP/NF | |
| Hydrocortisone 21-hemisuccinate sodium | Ph. Eur | Aventis, Switzerland (by Apoteksbolaget) |
| 2-OH-propyl-β-cyclodextrin | | |
| Hydroxypropylmethylcellulose | USP/NF | |
| Levomenthol | USP/NF | |
| Menthol | USP/NF | |
| Methocel E5 | Hydroxypropyl-methyl cellulose | Dow Chemicals, USA (by Colorcon) |
| Methocel ® KV 100 LV | USP/NF | Dow Chemicals, USA (by Colorcon) |
| Metolose ® | | |
| Microcrystalline cellulose, Avicel ® PH-102 | USP/NF | FMC Corporation |
| Paraffin powder | USP/NF | |
| PEG 300 | USP/NF | |
| PEG 6000 | Polyethylene glycol | Svenska Hoechst AB |
| PEG 400 | Polyethylene glycol | Fluka, Switzerland |
| Prednisolone | USP/NF | |
| Polyox WSR 301 | Polyethylene oxide | Dow Chemicals, USA |
| Na-alginate PH157 | | |
| Sodium dihydrogen phosphate | $NaH_2PO_4 \cdot 2\ H_2O$ | |
| Sodium stearyl fumarate | USP/NF | |
| Sorbitol | USP/NF | |
| Sugar | USP/NF | |
| Sugar/starch seeds | USP/NF | |
| Talc | USP/NF | |
| Triethyl citrate | USP/NF | |
| Xylitab 300 | | Xyrofin Kotka, Finland |
| Xylisorb 300 | | (Danisco Sweeteners Ltd, UK |
| Xylitol | USP/NF | Roquette, France |

Methods

The in vivo experiments reported herein were carried out on healthy volunteers. At 6 pm and 11 pm the day before administration of the test composition, the endogenous cortisol secretion was suppressed by oral administration of 2 mg of betamethasone. The test composition was administered to healthy volunteers. The volunteers were in fasted state and were not allowed to take any food until noon. In the case a tablet is administered, it is ingested together with 200 ml of water. The test composition is administered between 8 am and 10 am on the day following the suppression of endogenous glucocorticoid secretion.

EXAMPLES

Example 1

Capsules Containing an Immediate Release Pellets (IR Pellets)
IR Pellets

| Sugar/starch seeds, diameter 0.25-0.35 mm | 1 kg |
|---|---| are coated in a fluidised bed equipped with a Wurster column with a water suspension containing

| Hydrocortisone 21-hemisuccinate sodium | 10% |
|---|---|
| Hydroxypropyl methylcellulose, 6 cps | 3% |
| Talc | 10% |
| to a weight gain of approximately 75%. | |

An amount of IR pellets containing 13.4 mg of hydrocortisone 21-hemisuccinate sodium (approximately 70 mg) are filled into hard gelatine capsules size No 3 in a capsule-filling machine.

70 mg pellets will easily fit into a capsule size No. 3 (or even size No. 4) and can be filled in a normal capsule filling machine.

Example 2

Immediate Release (IR) Tablet
IR tablets for oral or sublingual use:

| | Mg per tablet |
|---|---|
| Betamethasone | 0.4 |
| Xylitab ® 300[a] | 40 |
| Lactose anhydrous USP/NF | 5 |
| Microcrystalline cellulose USP/NF | 10 |
| Crospovidone USP/NF | 4 |
| Sodium stearyl fumarate | 1 |
| Water | qs |

[a]Direct compression xylitol from Danisco Sweeteners Ltd UK

Dry mix lactose and microcrystalline cellulose. Dissolve betamethasone in a small amount of water and disperse the solution over the powder blend. Mix and dry. Add Xylitab and crospovidone and dry mix until the blend is homogeneous.

Add sodium stearyl fumarate and continue blending for another 2 minutes. Compress the blend to tablets in a tablet press using 6 mm round concave punches.

Example 3

Immediate Release (IR) Film
Thin films for administration to the oral cavity:

| | % by weight |
|---|---|
| Prednisolone | 0.75 |
| PEG 400 USP/NF | 2 |
| Methocel E5, Dow Chemical | 4 |
| Xylitol, Roquette France | 1 |
| Water | up to 100 |

Methocel was added to approximately 90% of the total amount of distilled water and stirred with a magnetic stirrer until Methocel was completely dissolved. PEG 400 was added under continued stirring, followed by xylitol and prednisolone. Water was added to final weight and stirring was continued during four hours.

330 µl of the solution was pipetted into 16 mm diameter flat-bottomed PVC blisters. The solutions were allowed to dry at room temperature over night and the blister packs were sealed with heat-seal lacquered aluminium foil.

Example 4

Immediate Release (IR) Oral Solution

| Oral solution: | |
|---|---|
| Prednisolone acetate | 0.9 mg |
| Sorbitol | 60 mg |
| Menthol | 1.2 mg |
| Sterile water | 5 ml |

Make a solution and fill into a moisture tight aluminium foliated sachet.

Example 5

Immediate Release (IR) Sublingual Spray
Sublingual spray of hydrocortisone:

| | mg/ml |
|---|---|
| Hydrocortisone acetate | 10 |
| Carboxymetylcellulose | 0.8 (0.08%) |
| 2-OH-propyl-β-cyclodextrin | 40 |
| PEG 300 | 5 |
| Menthol | 0.3 |
| Sorbitol | 12 |
| Levomenthol | 2.0 |
| $NaH_2PO_4 \cdot 2 H_2O$ | 2 |
| Water | qs |

Dissolve hydrocortisone acetate in a small amount of water. Mix with 2-OH-propyl-β-cyclodextrin, let stand for 1 hour. Add carboxymethylcellulose and mix. Add PEG 300, menthol, sorbitol, levomenthol and $NaH_2PO_4.2H_2O$. Add water up to final volume. Dispense into a spray package that delivers 0.58 ml per dose (5 mg of hydrocortisone).

Example 6

Betamethasone IR Tablet for Peroral or Buccal Administration

|  | Mg per tablet |
|---|---|
| Betamethasone | 0.4 |
| Xylitab ® 300[a] | 45 |
| Microcrystalline cellulose NF | 10 |
| Crospovidone NF | 4 |
| Water | qs |
| Sodium stearyl fumarate NF | 1 |

[a] Direct compression xylitol from Danisco Sweeteners Ltd, UK

Dissolve betamethasone in a small amount of water.

Disperse the solution over the microcrystalline cellulose. Mix and dry.

Add Xylitab and crospovidone and dry mix in a suitable mixer until a homogeneous blend is achieved.

Then add sodium stearyl fumarate and continue mixing another two minutes. Compress the powder blend in a suitable tablet press using 6 mm round concave punches.

Example 7

Sublingual Spray of Betamethasone

|  | mg/ml |
|---|---|
| Betamethasone | 0.4 |
| Carboxymetylcellulose | 0.8 (0.08%) |
| PEG 300 | 5 |
| Menthol | 0.3 |
| Sorbitol | 12 |
| Levomenthol | 2.0 |
| $NaH_2PO_4 \cdot 2H_2O$ | 2 |
| Water | qs |

Dissolve betamethasone in a small amount of water. Add carboxymethylcellulose and mix. Add PEG 300, menthol, sorbitol, levomenthol and $NaH_2PO_4 \cdot 2H_2O$. Add water up to final volume.

Example 8

Sublingual Spray of Betamethasone

|  | mg/ml |
|---|---|
| Betamethasone | 0.4 |
| Chitosan glutamate | 10 |
| Menthol | 0.1 |
| Levomenthol | 1.5 |
| $NaH_2PO_4 \cdot 2H_2O$ | 2 |
| Water | qs |

Dissolve betamethasone in a small amount of water. Add chitosan glutamate and mix. Filter through 0.2 μm membrane filter. Add menthol, levomenthol and $NaH_2PO_4 \cdot 2H_2O$. Add water up to final volume.

Example 9

Sublingual Spray of Hydrocortisone

|  | mg/ml |
|---|---|
| Hydrocortisone acetate | 10 |
| Carboxymetylcellulose | 0.8 (0.08%) |
| 2-OH-propyl-β-cyclodextrin | 40 |
| PEG 300 | 5 |
| Menthol | 0.3 |
| Sorbitol | 12 |
| Levomenthol | 2.0 |
| $NaH_2PO_4 \cdot 2H_2O$ | 2 |
| Water | qs |

Dissolve hydrocortisone in a small amount of water. Mix with 2-OH-propyl-β-cyclodextrin, let stand for 1 hour. Add carboxymethylcellulose and mix. Add PEG 300, menthol, sorbitol, levomenthol and $NaH_2PO_4 \cdot 2H_2O$. Add water up to final volume.

Example 10

Sublingual Spray of Hydrocortisone

|  | mg/ml |
|---|---|
| Hydrocortisone acetate | 10 |
| Chitosan glutamate | 10 |
| 2-OH-propyl-β-cyclodextrin | 40 |
| Menthol | 0.1 |
| Levomenthol | 1.5 |
| $NaH_2PO_4 \cdot 2H_2O$ | 2 |
| Water | qs |

Dissolve hydrocortisone in a small amount of water. Mix with 2-OH-propyl-β-cyclodextrin, let stand for 1 hour. Add chitosan glutamate and mix. Filter through 0.2 μm membrane filter. Add menthol, levomenthol and $NaH_2PO_4 \cdot 2H_2O$. Add water up to final volume.

Example 11

Thin-Layer Film of Hydrocortisone

|  | % w/w |
|---|---|
| Composition A: | |
| Hydrocortisone | 3% |
| Na-alginate PH157 | 2% |
| Water | 95% |
| Composition B: | |
| Hydrocortisone acetate | 3.4% |
| Na-alginate PH157 | 2% |
| Water | 94.6% |
| Composition C: | |
| Hydrocortisone | 3% |
| Metolose 60SH-50 | 2% |
| Water | 95% |

The films were made as described in the following:
1. Amount polymer, glucocorticoid and $H_2O$ were weighed.
2. The glucocorticoid was added to the water during stirring.
3. The formulation was kept on stirring until a suspension was obtained.

4. The polymer was added to the suspension.
5. The formulation was kept on stirring until a uniform gel was obtained (minimum 2 h).
6. 0.5 g gel was weighed in empty blisters and placed in a heating cupboard (Drying: 25° C. for 22 h).

Table. In vitro dissolution (rotating basket 100 rpm, phosphate buffer pH=7.0, one unit per 500 ml medium) after 1, 3, 5, 10 and 15 min as a percentage of 10 mg hydrocortisone. Units with 10 mg hydrocortisone in polymers of sodium alginate (Na-alg), hypromellose (HPMC) and approx. 7 mg/unit. Two units were tested with Na-alg and HPMC. The mean value is tabulated. The results in the following table reflect the rank order regarding viscosity, i.e. HPMC has the lowest viscosity and Na-alg the highest.

| Composition | Polymer | 1 min, % | 3 min, % | 5 min, % | 10 min, % | 15 min, % |
|---|---|---|---|---|---|---|
| A | Na-alg | 15 | 25 | 38 | 65 | 84 |
| B | Na-alg | 15 | 25 | 38 | 65 | 84 |
| C | HPMC | 18 | 48 | 67 | 88 | 92 |

In vivo plasma profiles in humans, N=1 per composition

Dexamethasone suppression test, fasting state, otherwise as described in the paragraph denoted "Method".

The results show that the use of hydrocortisone acetate does not seem to be suitable for an immediate release composition. This was further investigated in the following example.

Example 12

Non-Mucoadhesive Immediate Release Films

Two films were prepared essentially similar to Example 13—composition A. Film A contains 10 mg of hydrocortisone and film B contains 11.2 mg of hydrocortisone acetate. The results from in vivo testing after buccal administration are shown in FIGS. 4 and 5. The results show that even if the films are not bioadhesive, a fast onset of the absorption into the systemic circulation after single dose administration of Film A is obtained. In contrast, the results obtained with the film containing hydrocortisone acetate indicate that this compound does not seem to be suitable when a fast onset of the absorption into the systemic circulation of the glucocorticoid is required.

Example 13

Thin-Layer Films for Immediate Release

Batches of glucocorticoid films were prepared from the following compositions A and B:

| | Component | % w/w |
|---|---|---|
| Rapid-release composition A: | PEG 400 | 2.0 |
| | Hydrocortisone | 3.0 |
| | Methocel E5 | 4.0 |
| | Xylitol | 1.0 |
| | Water | 90 |
| Slower release composition B: | PEG 400 | 1.3 |
| | Hydrocortisone | 3.0 |
| | Methocel E5 | 5.7 |
| | Water | 90 |

To distilled water (18 ml) in 50 ml round-bottomed glass flask provided with a magnetic stirred was added Methocel E5. After the Methocel had dissolved completely PEG 400 was added under continued stirring, followed by xylitol (Composition A only) and hydrocortisone. Stirring was continued for 4 h.

Into flat-bottomed PVC-blisters (Inpack AB, Lund, Sweden) 16 mm in diameter was pipetted (Finnpipette; automatic) 330 μl of solution A or B into each blister trough. The solutions were allowed to dry at room temperature over night. The next day 10 films were removed for dose analysis. Each film was dissolved in 100 ml of water/ethanol (95%) 9:1 (w/w). The solutions were analysed by UV spectroscopy at 242 nm. Mean contents of 10.19 mg and 9.83 mg hydrocortisone per blister (SD 0.29 and 0.14, respectively) were found for Compositions A and B, respectively.

The hydrocortisone compositions were tested in two human subjects after labial administration. The subjects had their endogenous glucocorticoid secretion suppressed by synthetic glucocorticoids. The plasma concentration of cortisol was monitored during 360 min after the labial administration, and the serum concentration time profiles from these two subjects are shown in FIGS. 6 and 7.

It is clearly seen that the rate and extent of mucosal uptake of hydrocortisone is high and the appearance of cortisol in serum is rapid, as the first measured plasma concentration was attained already at 10-15 min.

These serum pharmacokinetic data illustrate that a formulation of the invention for oral mucosa administration results in a high rate and extent of mucosal absorption of the active drug, even though a small volume of fluid is available for dissolution at the site of administration and absorption in this route drug delivery.

Example 14

Glucocorticoid Tablets for Immediate Release

Glucocorticoid tablets were manufactured by direct compression of the dry-mixed powderous components to the following composition C:

| | Component | Per Batch |
|---|---|---|
| Rapid-release composition C: | PEG 6000 | 8.7 g |
| | Hydrocortisone | 2.5 g |
| | Xylitab 300 | 8.7 g |
| | Mg stearate | 0.16 g |

Batch Size 100 Tablets

The powderous components were sieved (mesh size 0.7 mm) and dry-mixed by shaking by hand in a small tin can for five min. The homogeneity of the mixture was analyzed by the same method as used for analysis of the tablets. Tabletting was carried out with a DIAF tabletting machine using a flat circular punch 7 mm in diameter (with a dividing score). The hydrocortisone dose in 10 tablets was assessed by the same method as used for the films. Mean contents of 9.53 mg hydrocortisone per tablet (SD 0.15) were found for composition C.

Tablet thickness (10 tablets): 1.72-1.76 mm (C);
Friability (20 tablets): 0.6% (C);
Tablet hardness (10 tablets): 23.7 N (C).

The compositions were tested after oral administration to two human subjects (see FIG. 8).

The rate of absorption of the glucocorticoid into the systemic circulation from the solid dosage forms of Example 14 was somewhat slower than that of compositions from Example 13, which means that it is possible to adjust the absorption rate of hydrocortisone into the systemic circulation by introducing changes in the composition and function of the labial pharmaceutical formulation.

Example 15

In Vitro Dissolution Profile

The in vitro dissolution profiles of hydrocortisone from drug formulations according to Example 20 and 21 were followed over time in a standardized controlled in vitro environment. A United States Pharmacopoeia dissolution apparatus II (paddle) coupled to automatic sampling devices and software was used for acquiring release profiles of the drug formulations in a neutral pH environment. The dissolution profile was acquired at 37° C., 50 rpm of the paddles, in a total of 300 ml of water. Sampling was performed at 0, 1, 3, 5, 7, 10 and 15 minutes following the insertion of the pharmaceutical composition in the example in the dissolution medium.

The dissolution profile from each formulation was monitored in two experiments up to 360 min after administration, and the corresponding dissolution time profiles are shown in FIGS. 9 and 10, respectively. The release rate is given as the percent of dose over time.

The release rate from the solid dosage forms of Example 21 was somewhat slower (FIG. 10). This means that it is possible to adjust the release rate of hydrocortisone by introducing changes in the composition and function of the oronasopharyngeal pharmaceutical preparation.

The invention claimed is:

1. A single-layer pharmaceutical composition in the form of a film, said composition consisting of one or more glucocorticoids and one or more bio/mucoadhesion promoting agents selected from sodium alginate and hydroxypropylmethylcellulose and, optionally, one or more taste masking agents selected from the group consisting of menthol, peppermint, vanillin, aspartame, and terpene based compounds, for administration to the oral mucosa of a subject for systemic delivery of the one or more glucocorticoids, for the treatment of a disorder requiring acute glucocorticoid therapy, said film being suitable for buccal administration, sublingual administration, palatal administration, or gingival administration,
    wherein at least about 60% of the one or more glucocorticoids are released from said film within the first 30 minutes after start of an in vitro dissolution test according to USP employing USP Dissolution Apparatus No. 2 (paddle), 50 rpm and a suitable dissolution medium.

2. The pharmaceutical composition according to claim 1 in unit dosage form.

3. The pharmaceutical composition according to claim 1, wherein the total amount of the one or more glucocorticoids expressed as hydrocortisone is from about 1 to about 200 mg.

4. The pharmaceutical composition according to claim 3, wherein the total amount of the one or more glucocorticoids expressed as hydrocortisone is from about 1 to about 175 mg, from about 1 to 150 mg, from about 1 to about 100 mg, from 1 to 75 mg, from about 1 to about 70 mg, from about 1 to about 60 mg, from about 5 to about 50 mg, from about 5 to about 40 mg, or from about 10 to about 30 mg.

5. The pharmaceutical composition according to claim 1, wherein the one or more glucocorticoids is selected from the group consisting of hydrocortisone, cortisone, prednisolone, prednisone, methylprednisone, triamcinolone, paramethasone, betamethasone, dexamethasone and fludrocortisone or mixtures thereof, including pharmaceutically acceptable esters thereof, and salts and other complexes of said esters.

6. The pharmaceutical composition according to claim 5, wherein the pharmaceutically acceptable salt or ester is a phosphate, a succinate, a lysinate, an acetate, a cypionate, a valerate, a hemisuccinate, a butyrate or a trometamole salt.

7. The pharmaceutical composition according to claim 1 in unit dosage form, wherein the one or more glucocorticoids are cortisone or hydrocortisone including pharmaceutically acceptable esters thereof, and salts and other complexes of said esters, and are present in an amount of from about 1-200 mg.

8. The pharmaceutical composition according to claim 1 in unit dosage form, wherein the one or more glucocorticoids are betamethasone including pharmaceutically acceptable esters thereof, and salts and other complexes of said esters, and are present in an amount of from about 1 to about 20 mg.

9. The pharmaceutical composition according to claim 1 in unit dosage form, wherein the one or more glucocorticoids are prednisolone including pharmaceutically acceptable esters thereof, and salts and other complexes of said esters, and are present in an amount of from about 1 to about 10 mg.

10. The pharmaceutical composition according to claim 1 in unit dosage form, wherein the one or more glucocorticoids are dexamethasone including pharmaceutically acceptable esters thereof, and salts and other complexes of said esters, and are present in an amount of from about 0.1 to about 2 mg.

11. The pharmaceutical composition according to claim 1 in unit dosage form, wherein the one or more glucocorticoids are fludrocortisone including pharmaceutically acceptable esters thereof, and salts and other complexes of said esters, and are present in an amount of from about 0.05 to about 5 mg.

12. The pharmaceutical composition according to claim 1 in unit dosage form, wherein the one or more glucocorticoids are prednisone including pharmaceutically acceptable esters thereof, and salts and other complexes of said esters, and are present in an amount of from about 10 to about 50 mg.

13. The pharmaceutical composition according to claim 1 in unit dosage form, wherein the one or more glucocorticoids are methylprednisolone including pharmaceutically acceptable esters thereof, and salts and other complexes of said esters, and are present in an amount of from about 2 to about 20 mg.

14. The pharmaceutical composition according to claim 1, wherein the one or more bio/mucoadhesion promoting agents are present in concentration of from about 0.1 to about 25% w/w.

15. The pharmaceutical composition according to claim 1, wherein the one or more glucocorticoids are present as microparticles or nanoparticles.

16. The pharmaceutical composition according to claim 15, wherein the mean particle size of the microparticles or nanoparticles is 10 um or less.

17. The pharmaceutical composition according to claim 1, said composition further comprising a taste-masking agent.

18. The pharmaceutical composition according to claim 1, formulated for buccal administration.

19. A method for treating a subject suffering from a disorder requiring acute glucocorticoid therapy, the method comprising: administering via the mucosa of the oral cavity of the subject an effective amount of a pharmaceutical composition as recited in claim 1 to obtain a glucocorticoid serum level of at least 20% of Cmax within 20 min after administration.

20. A method according to claim 19, wherein at least 40% of Cmax is reached within 30 min after administration.

21. A method according to claim 19, wherein at least 75% of Cmax is reached within 45 min after administration.

22. A method according to claim 19, wherein Tmax is reached within 60 min after administration of the composition via a mucosa of the subject.

23. A method according to claim 19, wherein the disorder requiring acute glucocorticoid therapy is an acute adrenal crisis.

24. A method according to claim 23, wherein the acute adrenal crisis relates to a primary, secondary, or tertiary adrenal insufficiency, an anaphylactic reaction, an Addison crisis, a status asthmaticus, a blood transfusion reaction, a brain edema, a severe allergic reaction, acute asthma, acute anaphylaxia, septic shock, acute bacterial meningitis, acute RSV (respiratory syncytial virus) infection with bronchiolitis in children, acute croup-children, mononucleosis with complications, or tonsillitis/peritonsillitis in children with airway obstruction.

25. A method according to claim 19, wherein the disorder requiring acute glucocorticoid therapy relates to an inflammatory disorder, an autoimmune disorder, or a medical disorder in which a glucocorticoid forms a part of the first line emergency medial treatment or intense short-time medical treatment.

26. A method according to claim 19, wherein the effective amount of the one or more glucocorticoids expressed as hydrocortisone is from about 1 to about 200 mg.

27. A method according to claim 26, wherein the effective amount of the one or more glucocorticoids expressed as hydrocortisone is from about 1 to about 175 mg such as, e.g., from about 1 to about 150 mg, from about 1 to about 125 mg, from about 1 to about 100 mg, from about 1 to about 75 mg, from about 1 to about 70 mg, from about 1 to about 60 mg, from about 5 to about 50 mg, from about 5 to about 40 mg or from about 10 to about 30 mg.

28. A method according to claim 19, wherein the one or more glucocorticoids is selected from the group consisting of hydrocortisone, cortisone, prednisolone, prednisone, methylprednisone, triamcinolone, paramethasone, betamethasone, dexamethasone and fludrocortisone or mixtures thereof, including pharmaceutically acceptable esters, salts and complexes thereof.

29. A method according to claim 28, wherein the pharmaceutically acceptable salt is a phosphate, a succinate, a lysinate, an acetate, a cypionate, a valerate, a hemisuccinate, a butyrate or a trometamole salt.

30. A method according to claim 19, wherein the effective amount of the one or more glucocorticoid is contained in a pharmaceutical composition suitable for administration by the subject itself or by non-medically trained persons.

31. A method according to claim 30, wherein the composition is in a form that can be administered to the subject even if he is unconscious.

32. A method according to claim 30, wherein the composition is in a form that can be administered to the subject and have effect even if he is unable to swallow the composition.

33. A method according to claim 19, wherein the one or more glucocorticoids are cortisone or hydrocortisone including pharmaceutically acceptable esters, salts and complexes thereof and wherein the effective amount is in a range of from about 1 to about 100 mg.

34. A method according to claim 19, wherein the one or more glucocorticoids are betamethasone including pharmaceutically acceptable esters, salts and complexes thereof and wherein the effective amount is in a range of from about 1 to about 20 mg.

35. A method according to claim 19, wherein the one or more glucocorticoids are prednisolone including pharmaceutically acceptable esters, salts and complexes and wherein the effective amount is in a range of from about 1 to about 10 mg.

36. A method according to claim 19, wherein the one or more glucocorticoids are dexamethsone including pharmaceutically acceptable esters, salts and complexes and wherein the effective amount is in a range of from about 0.1 to about 2 mg.

37. A method according to claim 19, wherein the one or more glucocorticoids are fludrocortisone including pharmaceutically acceptable esters, salts and complexes and wherein the effective amount is in a range of from about 0.05 to about 5 mg.

38. A method according to claim 19, wherein the one or more glucocorticoids are prednisone including pharmaceutically acceptable esters, salts and complexes and wherein the effective amount is in a range of from about 10 to about 50 mg.

39. A method according to claim 19, wherein the one or more glucocorticoids are methylprednisolone including pharmaceutically acceptable esters, salts and complexes and wherein the effective amount is in a range of from about 2 to about 20 mg.

40. A kit for treating a subject suffering from a disorder requiring acute glucocorticoid therapy comprising one or more containers for housing a pharmaceutical composition according to claim 1, and instructions for use thereof.

41. A kit according to claim 40, wherein the one or more containers are in the form of blisters or blister packs.

* * * * *